United States Patent

Suverkropp et al.

[11] Patent Number: 5,917,049
[45] Date of Patent: Jun. 29, 1999

[54] PROCESS FOR THE PREPARATION OF DICARBOXYLIC ACIDS

[75] Inventors: Geertrudes H Suverkropp, Geleen; Paulus L Alsters; Carina S Snijder, both of Sittard; Johannes G De Vries, Maastricht, all of Netherlands

[73] Assignee: DSM N.V., TE Heerlen, Netherlands

[21] Appl. No.: 08/989,404

[22] Filed: Dec. 12, 1997

[30] Foreign Application Priority Data

Dec. 16, 1996 [BE] Belgium ................................ 9601046

[51] Int. Cl.$^6$ ................................................. C07D 213/55
[52] U.S. Cl. ...................... 546/320; 548/334.5; 548/255
[58] Field of Search .................. 546/320; 548/334.5, 548/255

[56] References Cited

U.S. PATENT DOCUMENTS

| 4,537,971 | 8/1985 | Rebhahn et al. | 546/320 |
| 4,549,024 | 10/1985 | Orth et al. | 546/320 |
| 4,754,039 | 6/1988 | Michalowicz | 546/320 |

OTHER PUBLICATIONS

O'Murchu, "Ozonolysis of Quinolines: A Versatile Synthesis of Polyfunctional Pyridines", Synthesis, Journal of Synthetic Organic Chemistry, 1989 No. 11, Nov. pp. 880–992.

Chemical Abstracts, vol. 116, No. 12, 30 Maart 1992. Columbus, Ohio, US; abstract No. 128648y, Y. Furukawa et al.: "Preparation of quinolinic acid".

Primary Examiner—Jane Fan
Attorney, Agent, or Firm—Pillsbury Madison & Sutro LLP

[57] ABSTRACT

Process for the preparation of a heterocyclic o-dicarboxylic acid containing at least one N atom, in which a corresponding benzo-fused heterocyclic compound containing at least one N atom is oxidised in the presence of hydrogen peroxide, a Brönsted acid and an iron compound.

Preferably $Fe(NO_3)_3$ is used as the iron compound and $HNO_3$ as the Brönsted acid. The amount of iron compound to be used preferably lies between 0.1 and 2 mol. %, relative to the amount of employed benzo-fused heterocyclic compound containing at least one N atom. Even higher yields can be obtained if a copper compound or an organic electron-transferring compound is also used, in addition to the iron compound.

In particular, the process according to the invention can be used to prepare 2,3-pyridine dicarboxylic acids from corresponding quinoline compounds.

12 Claims, No Drawings

PROCESS FOR THE PREPARATION OF DICARBOXYLIC ACIDS

The invention relates to a process for the preparation of a heterocyclic o-dicarboxylic acid containing at least one N atom, in which a corresponding benzo-fused heterocyclic compound containing at least one N atom is oxidised in the presence of hydrogen peroxide, a metal compound and a Brönsted acid.

Such a process is known from U.S. Pat. No. 4,537,971, in which, in a multi-step process, copper sulphate is used as the metal salt and sulphuric acid as the Brönsted acid and in which copper quinolate is first prepared, which is subsequently, under basic conditions, converted into the Na salt of pyridine dicarboxylic acid, which is in turn subsequently converted into the free 2,3-pyridine dicarboxylic acid with the aid of HCl.

This known process is however rather laborious. Moreover, an equimolar amount of copper sulphate, relative to quinoline, is required to prepare the copper quinolate and a large amount of salt is formed in the process on account of the alternating basic and acid process conditions that have to be created in the preparation of the free 2,3-pyridine dicarboxylic acid.

The invention now provides a process that does not involve the aforementioned drawbacks.

This is achieved according to the invention by using an iron compound as the metal compound.

It has been found that a catalytic, substantially less than equimolar, amount of the iron compound suffices. Preferably the amount of iron compound is between 0.001 and 25 mol. %, relative to the amount of employed benzo-fused heterocyclic compound containing at least one N atom, in particular between 0.1 and 2 mol. %. Larger amounts are allowed in principle, but in practice they will no longer lead to a significant advantage.

As the iron compound use can for example be made of both Fe(II) and Fe(III) compounds, in particular all possible iron salts, for example iron salts of mineral acids. Particularly good results were obtained with $Fe(NO_3)_3$ and $FeSO_4$. The iron compound may optionally be formed in situ.

Preferably a copper compound or an organic electron-transferring compound is also used, in addition to the iron compound. It has been found that even higher yields can then be obtained. Both Cu(I) and Cu(II) compounds, in particular all possible copper salts, can be used as the copper compounds, for example copper salts of mineral acids, in particular $Cu(NO_3)_2$ and $CuSO_4$. The copper compound may optionally be formed in situ. Organic electron-transferring compounds are known to a person skilled in the art. Particularly good results were obtained with methyl viologene dichloride.

The amount of copper compound or organic electron-transferring compound to be used is not critical. The molar ratio of the copper compound or organic electron transferring compound to the iron compound preferably is between 10:1 and 1:10, particularly between 2:1 and 1:2.

The reaction is carried out in the presence of a—preferably strong—Brönsted acid, for example $HNO_3$, $H_2SO_4$, $H_3PO_4$ or a mixture of such acids. Preferably use is made of $HNO_3$, because that can easily be recovered by means of distillation, which means that the amount of salt produced can be reduced even further. The amount of Brönsted acid to be used preferably lies between 0.5 and 20, in particular between 1 and 5 acid equivalent(s), relative to the amount of employed benzo-fused heterocyclic compound containing at least one N atom. 'Acid equivalents' are in the context of this invention understood to be $H^+$ equivalents; 1 molar equivalent of sulphuric acid for example corresponds to 2 acid equivalents and 1 molar equivalent of $HNO_3$ to 1 acid equivalent. When $HNO_3$ is used as the Brönsted acid, this is for safety reasons preferably used as a 30–60 wt. % aqueous solution, while for example sulphuric acid or phosphoric acid is preferably used as a 5–100 wt. %, in particular as a 30–100 wt. %, (aqueous) solution.

The hydrogen peroxide ($H_2O_2$) is preferably used as an aqueous solution, the $H_2O_2$ concentration for example lying between 3 and 90 wt. %, in particular between 30 and 70 wt. %. Such solutions are readily available on a large scale. The amount of $H_2O_2$ to be used may vary within a wide range, the optimum amount may moreover vary from substrate to substrate. Preferably use is made of 1–40 molar equivalents of $H_2O_2$, relative to the amount of employed benzo-fused heterocyclic compound containing at least one N atom, in particular 5–10 molar equivalents.

In a suitable embodiment of the process according to the invention the iron compound and the Brönsted acid are introduced, after which the benzo-fused heterocyclic compound containing at least one N atom is added and, finally, the hydrogen peroxide is added. For safety reasons the hydrogen peroxide is preferably dosed in time, in particular so that the amount of $H_2O_2$ does not increase too much, preferably not further than 7% m/m hydrogen peroxide in the reaction mixture. The reaction can suitably be carried out in air, optionally it can be carried out in for example a nitrogen, oxygen or argon atmosphere.

Heterocyclic o-dicarboxylic acids that can be prepared using the process according to the invention are for example o-pyridine dicarboxylic acids, o-pyrimidine dicarboxylic acids, o-imidazole dicarboxylic acids and 1,2,3-triazole-o-dicarboxylic acids. Optionally, corresponding dimers, for example bipyridyl compounds (containing 4 carboxyl groups) can also be prepared.

The process according to the invention is for example very suitable for preparing 2,3-pyridine dicarboxylic acids which may or may not be substituted at their 4, 5 and/or 6 position(s). Examples of possible substituents are halogen, alkyl, alkoxyalkyl, carboxyl, sulphoxyl, nitro and phosphonate. The C-containing substituents preferably have 1–20 C atoms, in particular 1–8 C atoms. As the substrate use can then be made of quinoline compounds that have the same substituent(s) at their 2, 3 and/or 4 position(s), respectively, as the desired 2,3-pyridine dicarboxylic acid, and which may or may not be substituted with an alkoxy group at the starting material's 5 or 8 position and an alkyl or alkoxy group at the 6 or 7 position. The substituents preferably have 1–20 C atoms, in particular 1–8 C atoms. Preferably, non-substituted quinoline is however used at the 5, 6, 7 and 8 positions, because then the least amount of waste is released.

The temperature at which the oxidation reaction takes place preferably lies between 0 and 120° C., in particular between 20 and 100° C.

The invention will now be further elucidated with reference to the examples, without however being limited thereto.

EXAMPLE I 30 mg of $Fe(NO_3)_3 \cdot 9\, H_2O$ ($7.42 \cdot 10^{-5}$ mol) was dissolved in 15 g of $HNO_3$ (58% solution in water). 2.5 g (19.4 mmol) of quinoline was slowly added to this, with stirring. The whole was heated to 60° C. In 16 hours 20 ml of $H_2O_2$ (30% solution in water) was slowly added to the reaction mixture. After all the hydrogen peroxide had been added the reaction was continued for some time (about one hour typically).

HPLC analysis indicated that 2.04 g (63% yield) of 2,3-pyridine dicarboxylic acid had formed.

EXAMPLE II 60 mg of Fe(NO$_3$)$_3$.9 H$_2$O (1.49.10$^{-4}$ mol) was dissolved in 15 g of NHO$_3$ (58% solution in water). 2.75 g (19.2 mmol) of 3-methylquinoline was slowly added to this, with stirring. The whole was heated to 40° C. In 16 hours 20 ml of H$_2$O$_2$ (30% solution in water) was slowly added to the reaction mixture. After all the hydrogen peroxide had been added, the reaction was continued for some time (about one hour typically). HPLC analysis indicated that 1.91 g (55%) of 5-methyl-2,3-pyridine dicarboxylic acid had formed.

EXAMPLE III 10 mg of Fe(NO$_3$)$_3$.9 H$_2$O (2.1.10$^{-5}$ mol) and 5 mg of Cu(NO$_3$)$_2$ (2.48.10$^{-5}$ mol) were dissolved in 3 g of HNO$_3$ (58% solution in water). 592 mg (4.59 mmol) of quinoline was slowly added to this, with stirring. The whole was heated to 50° C. In 16 hours 4.7 ml of H$_2$O$_2$ (30% solution in water) was slowly added to the reaction mixture. After all the hydrogen peroxide had been added the reaction was continued for some time (about one hour typically). HPLC analysis indicated that 0.58 g (76%) of 2,3-pyridine dicarboxylic acid had formed.

EXAMPLES IV–VI

The results of the oxidation of a number of different substrates are given in the following table (Table 1); they were obtained in the same way as in Example I, except that an amount of 60 mg of Fe(NO$_3$)$_3$.9 H$_2$O was used and the reaction was carried out at 50° C.

TABLE 1

| Example | Substrate | Substrate (g) | H$_2$O$_2$ (ml) | HNO$_3$ (g) | Product | yield (%) |
| --- | --- | --- | --- | --- | --- | --- |
| IV | benz-imidazole | 0.457 | 4 | 3 | 4,5-imidazole dicarboxylic acid | 34 |
| V | isoquinoline | 0.501 | 4 | 3 | 3,4-pyridine dicarboxylic acid | 63 |
| VI | benzo-triazole | 0.461 | 4 | 3 | 1,2,3-triazole-4,5-dicarboxylic acid | 81 |

EXAMPLE VII 30 mg of Fe(NO$_3$)$_3$.9 H$_2$O (0.75.10$^{-4}$ mol) was dissolved in 15 g of H$_2$SO$_4$ (96% solution in water). 2.46 g (19.1 mmol) of quinoline was slowly added to this, with stirring. The whole was heated to 60° C. In 4 hours 12 ml of H$_2$O$_2$ (50% solution in water) was slowly added to the reaction mixture. After all the hydrogen peroxide had been added, the reaction was continued for some time (about one hour typically). HPLC analysis indicated that 2.36 g (74%) of 2,3-pyridine dicarboxylic acid had formed.

Comparative Experiment 6 mg of Cu(NO$_3$)$_2$ (2.98.10$^{-5}$ mol) was dissolved in 3 g of HNO$_3$ (58% solution in water). 522 mg (4.05 mmol) of quinoline was slowly added to this, with stirring. The whole was heated to 50° C. In 16 hours 4.3 ml of H$_2$O$_2$ (30% solution in water) was slowly added to the reaction mixture. After all the hydrogen peroxide had been added the reaction was continued for some time (about one hour typically). HPLC analysis indicated that 0.18 g (23%) of 2,3-pyridine dicarboxylic acid had formed.

EXAMPLE VIII 12 mg of Fe(NO$_3$)$_3$ (2.97×10$^{-5}$ mol) and 7 mg of methyl viologene dichloride (2.72×10$^{-5}$ mol) were dissolved in 3 g of HNO$_3$ (58 wt. % solution in water). 544 mg of quinoline (4.22 mmol) was slowly added to this solution, with stirring. The whole was heated to 50° C. In 16 hours 4.4 ml of H$_2$O$_2$ (30 wt. % solution in water) was slowly added to the reaction mixture. After all the hydrogen peroxide had been added the reaction was continued for some time (about one hour typically). HPLC analysis indicated that 0.51 g (72%) of 2,3-pyridine dicarboxylic acid had formed.

We claim:

1. A process for the preparation of an aromatic five or six membered heterocyclic o-dicarboxylic acid containing at least one N atom, wherein ring atoms which are not nitrogen are carbon, said process comprising oxidising a corresponding benzo-fused heterocyclic compound containing at least one N atom in the presence of hydrogen peroxide, an iron compound and a Brönsted acid.

2. The process according to claim 1, wherein said iron compound is Fe(NO$_3$)$_3$.

3. The process according to claim 1 or 2, wherein the iron compound is used in an amount of between 0.1 and 2 mol. %, relative to the amount of employed benzo-fused heterocyclic compound.

4. The process according to claim 1 or 2, wherein a copper compound is also present.

5. The process according to claim 1 or 2, wherein an organic electron transferring compound is also present.

6. The process according to claim 5, wherein the electron transferring compound is methyl viologene dichloride.

7. The process according to claim 1 or 2, wherein the Brönsted acid is HNO$_3$.

8. The process according to claim 1 or 2, wherein an optionally substituted 2,3-pyridine dicarboxylic acid is prepared from a corresponding quinoline compound.

9. The process according to claim 1 or 2, comprising the following sequential steps:

1) the iron compound and the Brönsted acid are introduced;
2) the benzo-fused heterocyclic compound is added; and
3) the hydrogen peroxide is added.

10. The process according to claim 9, wherein the hydrogen peroxide is dosed in time.

11. The process according to claim 1 or 2, wherein said benzo-fused heterocyclic compound is selected from the group consisting of benzimidazole, isoquinoline, benzotriazole, quinoline and 3-methylquinoline.

12. The process according to claim 1 or 2, wherein said heterocyclic o-dicarboxylic acid is an o-pyridine dicarboxylic acid, an o-pyrimidine dicarboxylic acid, an o-imidazole dicarboxylic acid or a 1, 2, 3 triazole-o-dicarboxylic acid.

* * * * *